(12) United States Patent
Sethi et al.

(10) Patent No.: US 9,687,161 B2
(45) Date of Patent: Jun. 27, 2017

(54) SYSTEMS AND METHODS FOR MAINTAINING BLOOD PRESSURE MONITOR CALIBRATION

(75) Inventors: Rakesh Sethi, Vancouver (CA); Shannon Campbell, Boulder, CO (US)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 2011 days.

(21) Appl. No.: 12/242,862

(22) Filed: Sep. 30, 2008

(65) Prior Publication Data

US 2010/0081945 A1   Apr. 1, 2010

(51) Int. Cl.
| | | |
|---|---|---|
| *A61B 5/021* | (2006.01) | |
| *A61B 5/02* | (2006.01) | |
| *A61B 5/024* | (2006.01) | |
| *A61B 5/1455* | (2006.01) | |
| *A61B 5/00* | (2006.01) | |

(52) U.S. Cl.
CPC .......... *A61B 5/021* (2013.01); *A61B 5/02007* (2013.01); *A61B 5/02108* (2013.01); *A61B 5/02416* (2013.01); *A61B 5/1455* (2013.01); *A61B 5/7257* (2013.01)

(58) Field of Classification Search
CPC ............................ A61B 5/021; A61B 5/02416
See application file for complete search history.

(56) References Cited

U.S. PATENT DOCUMENTS

| | | |
|---|---|---|
| 3,835,840 A | 9/1974 | Mount |
| 4,561,447 A | 12/1985 | Kawamura et al. |
| 4,676,253 A | 6/1987 | Newman et al. |
| 4,729,382 A | 3/1988 | Schaffer et al. |
| 4,830,017 A | 5/1989 | Perry et al. |
| 4,836,213 A | 6/1989 | Wenzel et al. |
| 4,854,327 A | 8/1989 | Kunig |
| 4,898,176 A | 2/1990 | Petre |
| 4,924,871 A | 5/1990 | Honeyager |
| 4,928,700 A | 5/1990 | Harada |
| 4,951,679 A | 8/1990 | Harada |
| 4,976,268 A | 12/1990 | Kurosawa et al. |
| 4,987,900 A | 1/1991 | Eckerle et al. |
| 5,065,765 A | 11/1991 | Eckerle et al. |
| 5,103,831 A | 4/1992 | Niwa |
| 5,105,815 A | 4/1992 | Hall et al. |
| 5,119,815 A | 6/1992 | Chance |

(Continued)

FOREIGN PATENT DOCUMENTS

| | | |
|---|---|---|
| EP | 0443267 | 8/1991 |
| EP | 0755221 | 1/1997 |

(Continued)

OTHER PUBLICATIONS

Bank, Alan J., Kaiser, Daniel R., "Smooth Muscle Relaxation: Effects on Arterial Compliance, Distensibility, Elastic modulus, and Pulse Wave Velocity," Hypertension, vol. 32, No. 2, Aug. 1998, pp. 356-359.

(Continued)

*Primary Examiner* — J. E. Angell
(74) *Attorney, Agent, or Firm* — Shvarts & Leiz LLP (57) ABSTRACT

Systems and methods are disclosed herein for maintaining the calibration of non-invasive blood pressure monitoring devices. Phase components of pulse signals detected by the blood pressure monitoring device are compared to stored baseline phase component values. If the difference exceeds a threshold, the blood pressure monitoring device is recalibrated.

21 Claims, 7 Drawing Sheets

(56) References Cited

U.S. PATENT DOCUMENTS

| | | |
|---|---|---|
| 5,119,824 A | 6/1992 | Niwa |
| 5,131,400 A | 7/1992 | Harada et al. |
| 5,163,328 A | 11/1992 | Holland et al. |
| 5,170,796 A | 12/1992 | Kobayashi |
| 5,176,143 A | 1/1993 | Eckerle et al. |
| 5,178,154 A | 1/1993 | Ackmann et al. |
| 5,179,956 A | 1/1993 | Harada et al. |
| 5,204,922 A | 4/1993 | Weir et al. |
| 5,238,000 A | 8/1993 | Niwa |
| 5,241,964 A | 9/1993 | McQuilkin |
| 5,255,686 A | 10/1993 | Takeda et al. |
| 5,269,312 A | 12/1993 | Kawamura et al. |
| 5,289,823 A | 3/1994 | Eckerle |
| 5,309,917 A | 5/1994 | Wang et al. |
| 5,431,159 A | 7/1995 | Baker et al. |
| 5,450,852 A | 9/1995 | Archibald et al. |
| 5,467,771 A | 11/1995 | Narimatsu et al. |
| 5,490,506 A | 2/1996 | Takatani et al. |
| 5,494,043 A | 2/1996 | O'Sullivan et al. |
| 5,497,779 A | 3/1996 | Takaya et al. |
| 5,505,209 A | 4/1996 | Reining |
| 5,533,511 A | 7/1996 | Kaspari et al. |
| 5,535,753 A | 7/1996 | Petrucelli et al. |
| 5,562,621 A | 10/1996 | Claude et al. |
| 5,564,427 A | 10/1996 | Aso et al. |
| 5,575,284 A | 11/1996 | Athan et al. |
| 5,617,868 A | 4/1997 | Harada et al. |
| 5,640,964 A | 6/1997 | Archibald et al. |
| 5,649,542 A | 7/1997 | Archibald et al. |
| 5,649,543 A | 7/1997 | Hosaka et al. |
| 5,676,140 A | 10/1997 | Ukawa et al. |
| 5,682,898 A | 11/1997 | Aung et al. |
| 5,685,316 A | 11/1997 | Schookin et al. |
| 5,704,362 A | 1/1998 | Hersh et al. |
| 5,709,212 A | 1/1998 | Sugo et al. |
| 5,720,292 A | 2/1998 | Poliac |
| 5,722,414 A | 3/1998 | Archibald et al. |
| 5,738,103 A | 4/1998 | Poliac |
| 5,743,856 A | 4/1998 | Oka et al. |
| 5,755,669 A | 5/1998 | Ono et al. |
| 5,762,610 A | 6/1998 | Narimatsu et al. |
| 5,772,601 A | 6/1998 | Oka et al. |
| 5,772,602 A | 6/1998 | Sakai et al. |
| 5,776,071 A | 7/1998 | Inukai et al. |
| 5,785,659 A | 7/1998 | Caro et al. |
| 5,791,347 A | 8/1998 | Flaherty et al. |
| 5,797,395 A | 8/1998 | Martin |
| 5,797,850 A | 8/1998 | Archibald et al. |
| 5,810,736 A | 9/1998 | Pail |
| 5,827,181 A | 10/1998 | Dias et al. |
| 5,830,131 A | 11/1998 | Caro et al. |
| 5,832,924 A | 11/1998 | Archibald et al. |
| 5,833,618 A | 11/1998 | Caro et al. |
| 5,848,970 A | 12/1998 | Voss et al. |
| 5,857,975 A | 1/1999 | Golub |
| 5,873,834 A | 2/1999 | Yanagi et al. |
| 5,904,654 A | 5/1999 | Wohltmann et al. |
| 5,941,828 A | 8/1999 | Archibald et al. |
| 5,964,711 A | 10/1999 | Voss et al. |
| 6,002,952 A | 12/1999 | Diab et al. |
| 6,004,274 A | 12/1999 | Nolan et al. |
| 6,007,492 A | 12/1999 | Goto et al. |
| 6,011,986 A | 1/2000 | Diab et al. |
| 6,022,320 A | 2/2000 | Ogura et al. |
| 6,027,452 A | 2/2000 | Flaherty et al. |
| 6,027,453 A | 2/2000 | Miwa et al. |
| 6,027,455 A | 2/2000 | Inukai et al. |
| 6,045,509 A | 4/2000 | Caro et al. |
| 6,067,462 A | 5/2000 | Diab et al. |
| 6,083,171 A | 7/2000 | Ono et al. |
| 6,095,987 A | 8/2000 | Shmulewitz et al. |
| 6,135,966 A | 10/2000 | Ko |
| 6,157,850 A | 12/2000 | Diab et al. |
| 6,159,157 A | 12/2000 | Archibald et al. |
| 6,161,038 A | 12/2000 | Schookin et al. |
| 6,186,954 B1 | 2/2001 | Narimatsu |
| 6,186,955 B1 | 2/2001 | Baura |
| 6,190,382 B1 | 2/2001 | Ormsby et al. |
| 6,196,974 B1 | 3/2001 | Miwa |
| 6,217,524 B1 | 4/2001 | Orr et al. |
| 6,227,196 B1 | 5/2001 | Jaffe et al. |
| 6,228,034 B1 | 5/2001 | Voss et al. |
| 6,241,661 B1 | 6/2001 | Schluess et al. |
| 6,241,679 B1 | 6/2001 | Curran |
| 6,245,022 B1 | 6/2001 | Archibald et al. |
| 6,251,081 B1 | 6/2001 | Narimatsu |
| 6,263,222 B1 | 7/2001 | Diab et al. |
| 6,292,689 B1 | 9/2001 | Wallace et al. |
| 6,293,915 B1 | 9/2001 | Amano et al. |
| 6,299,582 B1 | 10/2001 | Brockway et al. |
| 6,332,867 B1 | 12/2001 | Chen et al. |
| 6,350,242 B1 | 2/2002 | Doten et al. |
| 6,371,921 B1 | 4/2002 | Caro et al. |
| 6,443,905 B1 | 9/2002 | Nissila et al. |
| 6,463,311 B1 | 10/2002 | Diab |
| 6,471,646 B1 | 10/2002 | Thede |
| 6,471,655 B1 | 10/2002 | Baura |
| 6,506,161 B2 | 1/2003 | Brockway et al. |
| 6,514,211 B1 | 2/2003 | Baura |
| 6,524,240 B1 | 2/2003 | Thede |
| 6,549,284 B1 | 4/2003 | Boas et al. |
| 6,561,986 B2 | 5/2003 | Baura et al. |
| 6,589,185 B1 | 7/2003 | Archibald et al. |
| 6,599,251 B2 | 7/2003 | Chen et al. |
| 6,602,199 B2 | 8/2003 | Chen et al. |
| 6,602,201 B1 | 8/2003 | Hepp et al. |
| 6,606,511 B1 | 8/2003 | Ali et al. |
| 6,626,839 B2 | 9/2003 | Doten et al. |
| 6,631,281 B1 | 10/2003 | Kastle |
| 6,632,181 B2 | 10/2003 | Flaherty et al. |
| 6,645,156 B2 | 11/2003 | Oka |
| 6,658,277 B2 | 12/2003 | Wasserman |
| 6,684,090 B2 | 1/2004 | Ali et al. |
| RE38,476 E | 3/2004 | Diab et al. |
| 6,699,194 B1 | 3/2004 | Diab et al. |
| 6,767,328 B2 | 7/2004 | Kulik |
| 6,773,397 B2 | 8/2004 | Kelly |
| 6,783,498 B2 | 8/2004 | Sackner et al. |
| 6,816,741 B2 | 11/2004 | Diab |
| 6,822,564 B2 | 11/2004 | Al-Ali |
| 6,826,419 B2 | 11/2004 | Diab et al. |
| 6,827,688 B2 | 12/2004 | Goto et al. |
| 6,852,083 B2 | 2/2005 | Caro et al. |
| 6,855,112 B2 | 2/2005 | Kao et al. |
| 6,863,652 B2 | 3/2005 | Huang et al. |
| 6,869,403 B2 | 3/2005 | Narimatsu et al. |
| 6,929,610 B2 | 8/2005 | Forstner |
| 6,996,427 B2 | 2/2006 | Ali et al. |
| 7,004,907 B2 | 2/2006 | Banet et al. |
| 7,043,293 B1 | 5/2006 | Baura |
| 7,044,918 B2 | 5/2006 | Diab |
| 7,070,566 B2 | 7/2006 | Medero et al. |
| 7,074,192 B2 | 7/2006 | Friedman et al. |
| 7,079,035 B2 | 7/2006 | Bock et al. |
| 7,087,025 B2 | 8/2006 | Baruch |
| 7,184,809 B1 | 2/2007 | Sterling et al. |
| 7,215,984 B2 | 5/2007 | Diab et al. |
| 7,215,986 B2 | 5/2007 | Diab et al. |
| 7,252,636 B2 | 8/2007 | Brown |
| 7,320,030 B2 | 1/2008 | Brown |
| 7,335,162 B2 | 2/2008 | Eide |
| 7,376,238 B1 | 5/2008 | Rivas et al. |
| 7,390,300 B2 | 6/2008 | Inukai et al. |
| 7,390,301 B2 | 6/2008 | Skrabal et al. |
| 7,393,327 B2 | 7/2008 | Inukai et al. |
| 7,400,257 B2 | 7/2008 | Rivas |
| 7,455,643 B1 | 11/2008 | Li et al. |
| 7,481,772 B2 | 1/2009 | Banet |
| 7,485,095 B2 | 2/2009 | Shusterman |
| 2005/0148885 A1 | 7/2005 | Tweed et al. |
| 2005/0192500 A1 | 9/2005 | Caro et al. |
| 2005/0228297 A1 | 10/2005 | Banet et al. |
| 2005/0251344 A1 | 11/2005 | Appel et al. |
| 2005/0261594 A1 | 11/2005 | Banet |

(56) References Cited

U.S. PATENT DOCUMENTS

| | | |
|---|---|---|
| 2006/0009700 A1 | 1/2006 | Brumfield et al. |
| 2006/0063992 A1 | 3/2006 | Yu et al. |
| 2006/0063993 A1 | 3/2006 | Yu et al. |
| 2006/0079945 A1 | 4/2006 | Libbus |
| 2006/0206021 A1 | 9/2006 | Diab |
| 2006/0217614 A1 | 9/2006 | Takala et al. |
| 2006/0217628 A1 | 9/2006 | Huiku |
| 2006/0241975 A1 | 10/2006 | Brown |
| 2006/0285736 A1 | 12/2006 | Brown |
| 2006/0287590 A1 | 12/2006 | McEowen |
| 2006/0287603 A1 | 12/2006 | Bartnik et al. |
| 2007/0055163 A1 | 3/2007 | Asada et al. |
| 2007/0066910 A1 | 3/2007 | Inukai et al. |
| 2007/0083093 A1 | 4/2007 | Diab |
| 2007/0118045 A1 | 5/2007 | Naghavi et al. |
| 2007/0225582 A1 | 9/2007 | Diab et al. |
| 2007/0225606 A1 | 9/2007 | Naghavi et al. |
| 2007/0249467 A1 | 10/2007 | Hong et al. |
| 2008/0015451 A1 | 1/2008 | Hatib et al. |
| 2008/0030468 A1 | 2/2008 | Ali et al. |
| 2008/0033305 A1 | 2/2008 | Hatib et al. |
| 2008/0132798 A1 | 6/2008 | Hong et al. |
| 2008/0214903 A1 | 9/2008 | Orbach |
| 2008/0214942 A1 | 9/2008 | Oh et al. |
| 2008/0242955 A1 | 10/2008 | Uutela et al. |
| 2009/0048497 A1 | 2/2009 | Keren |

FOREIGN PATENT DOCUMENTS

| | | |
|---|---|---|
| GB | 2356250 | 5/2001 |
| GB | 2356251 | 5/2001 |
| GB | 2356252 | 5/2001 |
| JP | 03225268 | 10/1991 |
| JP | 03231630 | 10/1991 |
| JP | 06142082 | 5/1994 |
| JP | 07136136 | 5/1995 |
| WO | 0132076 A | 5/2001 |

OTHER PUBLICATIONS

Berne, Robert M., Levy, Matthew N., eds., Physiology, 2nd edition, St. Louis, Mosby, 1988, pp. 357-681.

Finkelstein, Stanley M., Cohn, Jay N., "First- and Third-Order Models for Determining Arterial Compliance," Journal of Hypertension, vol. 10, supplement 6, Aug. 1992, pp. 511-514.

Fitchett, D., Bouthier, JD, Simon, A. Ch., Levenson, JA, Safar, ME, "Forearm Arterial Compliance: The Validation of a Plethysmographic Technique for the Measurement of Arterial Compliance," Clinical Science, vol. 67, No. 1, Jul. 1984, pp. 69-72.

Fletcher, Gerald F., ed., Cardiovascular Response to Exercise, Mt. Kisco, NY, Futura Publishing Co., 1994.

Fung, YC, Biomechanics: Circulation, 2nd Edition, New York, Springer, 1997.

Geddes, LA, Handbook of Blood Pressure Measurement, Clifton, New Jersey, Humana Press, 1991.

Millasseau, Sandrine C, Guigui, Franck G, Kelly, Ronan P., Prasad, Krishna, Cockcroft, John R., Ritter, James M., Chowienczyk, Philip J., Noninvasive Assessment of the Digital Volume Pulse: Comparison with the Peripheral Pressure Pulse, Hypertension, vol. 36, No. 6, Dec. 2000, pp. 952-956.

Moyle, John TB, Hahn, CEW, Adams, Anthony P, Pulse Oximetry, Revised Edition, London, BMJ, 1998.

Nara, Andrew R., Burns, Michael P., Downs, W. Gregory, Blood Pressure, Redmond, Washington, SpaceLabs, 1989.

Nichols, Wilmer W., O'Rourke, Michael F., McDonald's Blood Flow in Arteries: Theoretic, Experimental, and Clinical Principles, 3rd Edition, Philadelphia, Lea & Febiger, 1990.

O'Rourke, Michael F., Gallagher, David E., "Pulse Wave Analysis," Journal of Hypertension, vol. 14, supplement 5, Dec. 1996, pp. S147-S157.

Takazawa, Kenji, Tanaka, Nobuhiro, Fujita, Masami, Matsuoka, Osamu, Saiki, Tokuyu, Aikawa, Masaru, Tamura, Sinobu, Ibukiyama, Chiharu, "Assessment of Vasoactive Agents and Vascular Aging by the Second Derivative of Photoplethysmogram Waveform," Hypertension, vol. 32, No. 2, Aug. 1998, pp. 365-370.

Tardy, Y, Meister, JJ, Perret F, Brunner, HR, Arditi, M, "Non-Invasive Estimate of the Mechanical Properties of Peripheral Arteries from Ultrasonic and Photoplethysmographic Measurements," Clinical Physics and Physiological Measurement, vol. 12, No. 1, pp. 39-54, Feb. 1991.

Young, Christopher C., Mark, Jonathan B., White, William, DeBree, Ashley, Vender, Jeffery S., Fleming, Andrew, "Clinical Evaluation of Continuous Noninvasive Blood Pressure Monitoring: Accuracy and Tracking Capabilities," Journal of Clinical Monitoring, vol. 11, No. 4, Jul. 1995, pp. 245-252.

Quick et al. Apparent Arterial Compliance. Am J Physiol Heart Circ Physiol 274:1393-1403, 1998.

Foo et al. Use of Pulse Transmit Time to Differentiate Central From Obstructive Respiratory Events in Sleeping Infants. Australas. Phys. Eng. Sci. Med. 27:4, 2004. Proc. of EPSM 2004.

Foo et al. Pulse Transit Time to Monitor Changes in Peripheral Pulse Timing Characteristics of Children. Australas. Phys. Eng. Sci. Med. 27:4, 2004. Proc. of EPSM 2004.

Manwaring et al. A Signal Analysis Algorithm for Determining Brain Compliance Non-Invasively. Proc. of the 26th Annual International Conference of the IEEE EMBS, San Francisco, CA, USA. Sep. 1-5, 2004.

International Search Report PCT/IB2009/006891/006138, 4 pages, mailed Dec. 23, 2009.

SYSTEMS AND METHODS FOR MAINTAINING BLOOD PRESSURE MONITOR CALIBRATION

SUMMARY

In accordance with various embodiments, monitoring blood pressure non-invasively proves susceptible to reduced precision resulting from changes in arterial compliance. In accordance with various embodiments, such reduced precision can be avoided by monitoring arterial compliance indicators and recalibrating a blood pressure monitoring device in response to indications of significant arterial compliance changes.

According to an aspect, the disclosure relates to a blood pressure monitor. The blood pressure monitor includes one or more sensors, for example, a pulse oximeter, for detecting a pulse signal from a patient. The blood pressure monitor also includes a memory for storing a baseline pulse signal phase component and a processor. The processor is capable of storing a first baseline pulse signal phase component in the memory derived from a pulse signal obtained at about a calibration time. The processor is also capable of monitoring a current phase component of the pulse signal over a period of time subsequent to the calibration time. The processor calculates a difference between the current phase component and the stored baseline phase component. The processor then triggers a recalibration of the blood pressure monitor in response to the calculated difference exceeding a threshold.

In an embodiment, calculating the difference between the current phase component with the stored baseline phase component comprises calculating the difference between the phase components at a signal frequency of less than about 10 Hz. In another embodiment, calculating the difference between the current phase component with the stored baseline phase component comprises calculating the difference between the phase components at a signal frequency of less than about 5 Hz. The phase components are obtained, in one embodiment, by calculating the Fourier phase component of the pulse signals.

In an embodiment, the blood pressure monitor includes an input for receiving a calibration blood pressure measurement at about the calibration time from an external blood pressure sensor. The calibration blood pressure measurement, along with the pulse signal(s) obtained at the calibration time, may be used by the processor to calibrate the blood pressure monitor.

In an embodiment, the processor is capable of obtaining a second calibration blood pressure value at a second calibration time. The processor calculates blood pressure calibration values based on a pulse signal obtained at about the second calibration time and the second calibration blood pressure measurement and stores an updated baseline pulse signal phase component based on the calculation.

According to an aspect, the disclosure relates to a method of monitoring blood pressure. The method includes storing a baseline pulse signal phase component associated with a pulse signal, e.g., a pleth signal, obtained at a calibration time. Subsequently, current phase components of the pulse signal are monitored over time. Differences between the current phase components and the stored baseline components are compared to a threshold. If the difference exceeds the threshold, the method includes triggering a recalibration of a pulse-signal based blood pressure monitor.

In an embodiment, the method includes receiving a calibration blood pressure value derived at about the calibration time. The calibration blood pressure value, in one embodiment, is determined independent of the pulse signal data.

In an embodiment, in response to the calculated difference falling below the threshold, the method includes calculating a monitored blood pressure value using a pulse signal at a time subsequent to the calibration time.

According to an aspect, the disclosure relates to a computer-readable medium for use in maintaining the calibration of a blood pressure monitor. The computer-readable medium has computer program instructions recorded thereon for storing a baseline pulse signal phase component associated with a pleth signal obtained at a calibration time and monitoring a current phase component of the pleth signal over a period of time subsequent to the calibration time. The computer-readable medium also has computer program instructions for calculating a difference between the current phase component with the stored baseline phase component and triggering a recalibration of a pleth signal-based blood pressure monitor in response to the calculated difference exceeding a threshold.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. In addition, locations which are not typically understood to be optimal for pulse oximetry serve as suitable sensor locations for the blood pressure monitoring processes described herein, including any location on the body that has a strong pulsatile arterial flow. For example, additional suitable sensor locations include, without limitation, the neck to monitor cartoid artery pusatile flow, the wrist to monitor radial artery pulsatile flow, the inside of a patient's thigh to monitor femural artery pulsatile flow, the ankle to monitor tibial artery pulsatile flow, and around or in front of the ear. Suitable sensors for these locations may include sensors for sensing absorbed light based on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof a log taken thereof a scaled version of a log taken thereof etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

Figure 1:
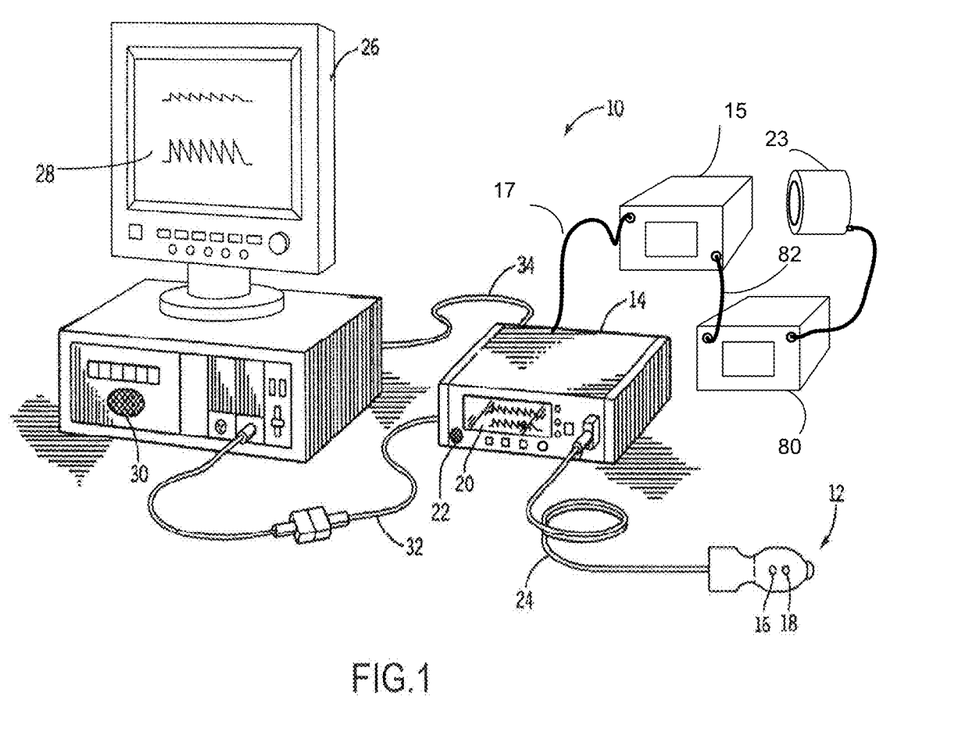
FIG. 1 shows an illustrative pulse oximetry system in accordance with an embodiment.

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to an embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In an embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range. In an embodiment, the monitor 14 includes a blood pressure monitor 15. In alternative embodiments, the pulse oximetry system 10 includes a stand alone blood pressure monitor 15 in communication with the monitor 14 via a cable 17 or a wireless network link.

In an embodiment, sensor 12, or the sensor array, may be communicatively coupled to monitor 14 via a cable 24. However, in other embodiments, a wireless transmission device (not shown) or the like may be used instead of or in addition to cable 24.

In an embodiment, pulse oximetry system 10 may also include a multi-parameter patient monitor 26. The monitor may be a cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "SpO$_2$" measurement), pulse rate information from monitor 14 and blood pressure from the blood pressure monitor 15 on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Calibration device 80, which may be powered by monitor 14, a battery, or by a conventional power source such as a wall outlet, may include any suitable blood pressure calibration device. For example, calibration device 80 may take the form of any invasive or non-invasive blood pressure monitoring or measuring system used to generate reference blood pressure measurements for use in calibrating the CNIBP monitoring techniques described herein. Such calibration devices may include, for example, an aneroid or mercury sphygmomanometer and occluding cuff 23, a pressure sensor inserted directly into a suitable artery of a patient, an oscillometric device or any other device or mechanism used to sense, measure, determine, or derive a reference blood pressure measurement. In some embodiments, calibration device 80 may include a manual input device (not shown) used by an operator to manually input reference blood pressure measurements obtained from some other source (e.g., an external invasive or non-invasive blood pressure measurement system).

Calibration device 80 may also access reference blood pressure measurements stored in memory (e.g., RAM, ROM, or a storage device). For example, in some embodiments, calibration device 80 may access reference blood pressure measurements from a relational database stored within calibration device 80, monitor 14, or multi-parameter patient monitor 26. The reference blood pressure measurements generated or accessed by calibration device 80 may be updated in real-time, resulting in a continuous source of reference blood pressure measurements for use in continuous or periodic calibration. Alternatively, reference blood pressure measurements generated or accessed by calibration device 80 may be updated periodically, and calibration may be performed on the same periodic cycle. Preferably, the reference blood pressure measurements are generated when recalibration is triggered as described below. In the depicted embodiments, calibration device 80 is connected to monitor 14 or blood pressure monitor 15 via cable 82. In other embodiments, calibration device 80 may be a stand-alone device that may be in wireless communication with monitor 14. Reference blood pressure measurements may then be wirelessly transmitted to monitor 14 for use in calibration. In still other embodiments, calibration device 80 is completely integrated within monitor.

Figure 2:
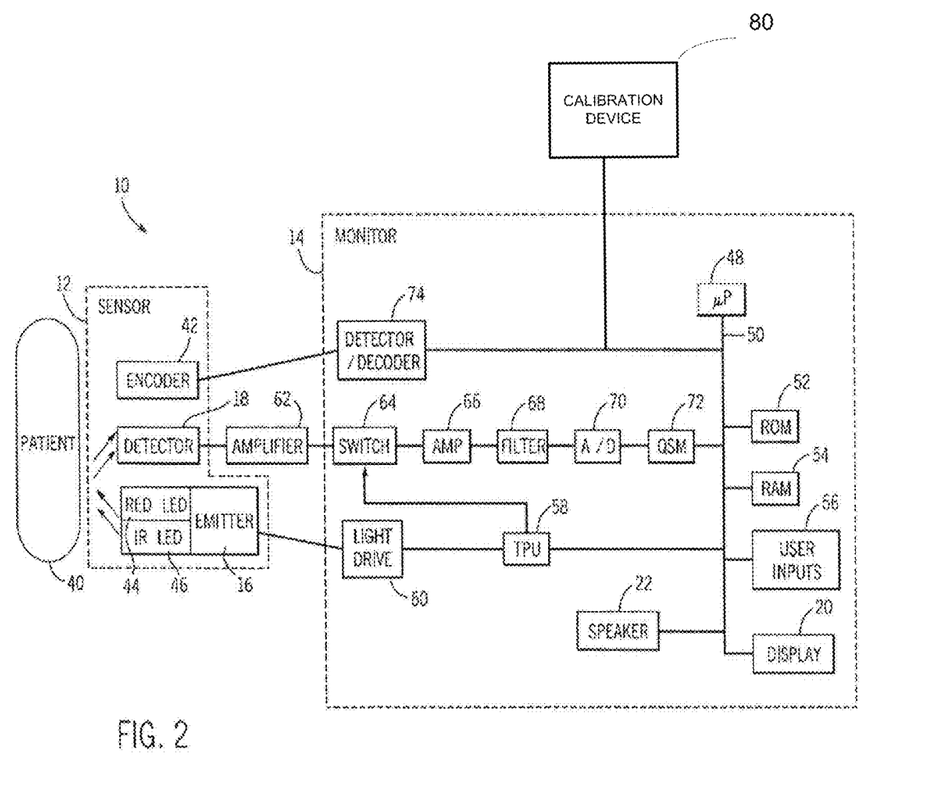
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light. In another example, the wavelengths of light used are selected based on the specific location of the sensor.

It will be understood that) as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed, reflected, or scattered, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In an embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In an embodiment, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

Figure 3:
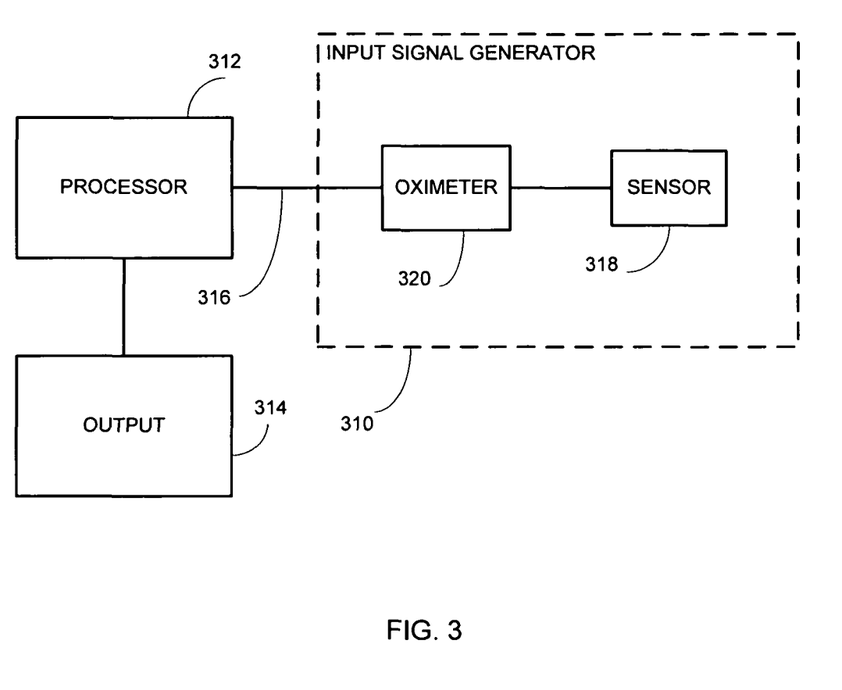
FIG. 3 is a block diagram of an illustrative signal processing system in accordance with some embodiments.

FIG. 3 is an illustrative signal processing system in accordance with an embodiment. In this embodiment, input signal generator 310 generates an input signal 316. As illustrated, input signal generator 310 may include oximeter 320 coupled to sensor 318, which may provide as input signal 316, a PPG signal. It will be understood that input signal generator 310 may include any suitable signal source, signal generating data, signal generating equipment, or any combination thereof to produce signal 316. Signal 316 may be any suitable signal or signals, such as, for example, biosignals that represent a patient's pulse.

In an embodiment, signal 316 may be coupled to processor 312. Processor 312 may be any suitable software, firmware, and/or hardware, and/or combinations thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may perform the calculations associated with the signal processing of the present disclosure as well as the calculations associated with any suitable interrogations of the processed signals. Processor 312 may perform any suitable signal processing of signal 316 to filter signal 316, such as any suitable band-pass filtering, adaptive filtering, closed-loop filtering, and/or any other suitable filtering, and/or any combination thereof.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may also be used by the processor 312 to store blood pressure monitoring data, including current blood pressure calibration values, blood pressure monitoring calibration thresholds, and patient blood pressure history.

Processor 312 may be coupled to output 314. Output 314 may be any suitable output device such as, for example, one or more medical devices (e.g., a medical monitor that displays various physiological parameters, a medical alarm, or any other suitable medical device that either displays physiological parameters or uses the output of processor 312 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 300 may be incorporated into system 10 (FIGS. 1 and 2) in which, for example, input signal generator 310 may be implemented as parts of sensor 12 and monitor 14 and processor 312 may be implemented as part of monitor 14.

Pulse oximeters, in addition to providing other information, can be utilized to determine the blood pressure of a patient. As described in U.S. Pat. No. 6,599,251, the entirety of which is incorporated herein by reference, PPG and other pulse signals obtained from multiple probes can be processed to calculate the blood pressure of a patient. In particular, blood pressure is derived based on a comparison of time delays between certain components of the pulse signals detected at each of the respective probes. As described in U.S. patent application Ser. No. 12/242,238, entitled "Systems and Methods For Non-Invasive Blood Pressure Monitoring," and filed on Sep. 30, 2008, the entirety of which is incorporated herein by reference, blood pressure can also be derived by processing time delays detected within a single PPG or pulse signal obtained from a single pulse oximeter probe. In addition, as described in U.S. patent application Ser. No. 12/242,867, entitled "Systems and Methods For Non-Invasive Continuous Blood Pressure Determination," and filed on Sep. 30, 2008, the entirety of which is incorporated herein by reference, blood pressure may also be obtained by calculating the area under certain portions of a pulse signal.

One benefit of monitoring blood pressure based on pulse signals is that such signals can be obtained in a non-invasive fashion. To continuously monitor blood pressure using a conventional sphygmomanometer, a cuff is repeatedly inflated around a patient's appendage, applying significant pressure. Such repeated pressure can result at a minimum in patient discomfort and potentially in serious injury. In contrast, continuous blood pressure monitoring based on a pulse signal may be achieved merely by placing a pulse oximetry probe on an appendage or other part of a patient's body.

Several pulse signal-based blood pressure monitoring techniques are based on calibration blood pressure data collected in a more invasive fashion, for example via a sphygmomanometer. That is, data derived from the pulse signal at a calibration time is compared to a blood pressure reading obtained in a more conventional, invasive fashion. For this calibration to remain accurate, preferably certain physiological characteristics of the patient, including the compliance of the patient's arteries, must remain relatively constant. Significant changes in these characteristics may result in less accurate blood pressure readings, making recalibration desirable.

In general, the methodologies referenced above rely in part on determining or estimating pulse wave propagation rates, including initial pulse wave propagation and/or reflection rates. One determinant of pulse wave propagation and reflection rates is the compliance or alternatively, the elasticity, of the arteries of the patient. Thus, compliance changes may alter apparent blood pressure, (i.e., blood pressure determined based on a pulse signal). In addition, compliance has a direct impact on actual blood pressure. Specifically, all other things remaining constant, increased compliance results in larger blood pressure changes for a given volume change. That is, the difference between systolic and diastolic pressure will be larger. Decreased compliance results in a decrease in blood pressure change for a given volume change. That is, the difference between systolic and diastolic pressure will be smaller. However, the impact of compliance on apparent blood pressure often differs from the impact of compliance on actual blood pressure. As keeping a patients arterial compliance constant may not be possible, practical, or even desired, it is desirable to have a pulse signal-based blood pressure monitor take arterial compliance into account in determining blood pressure. One way of taking arterial compliance into account is to monitor compliance and recalibrate the blood pressure monitor upon detection of significant changes in compliance, thereby reducing calibration errors as well as unnecessary recalibrations. Detected compliance changes may also be used directly for recalibration.

Figure 4:
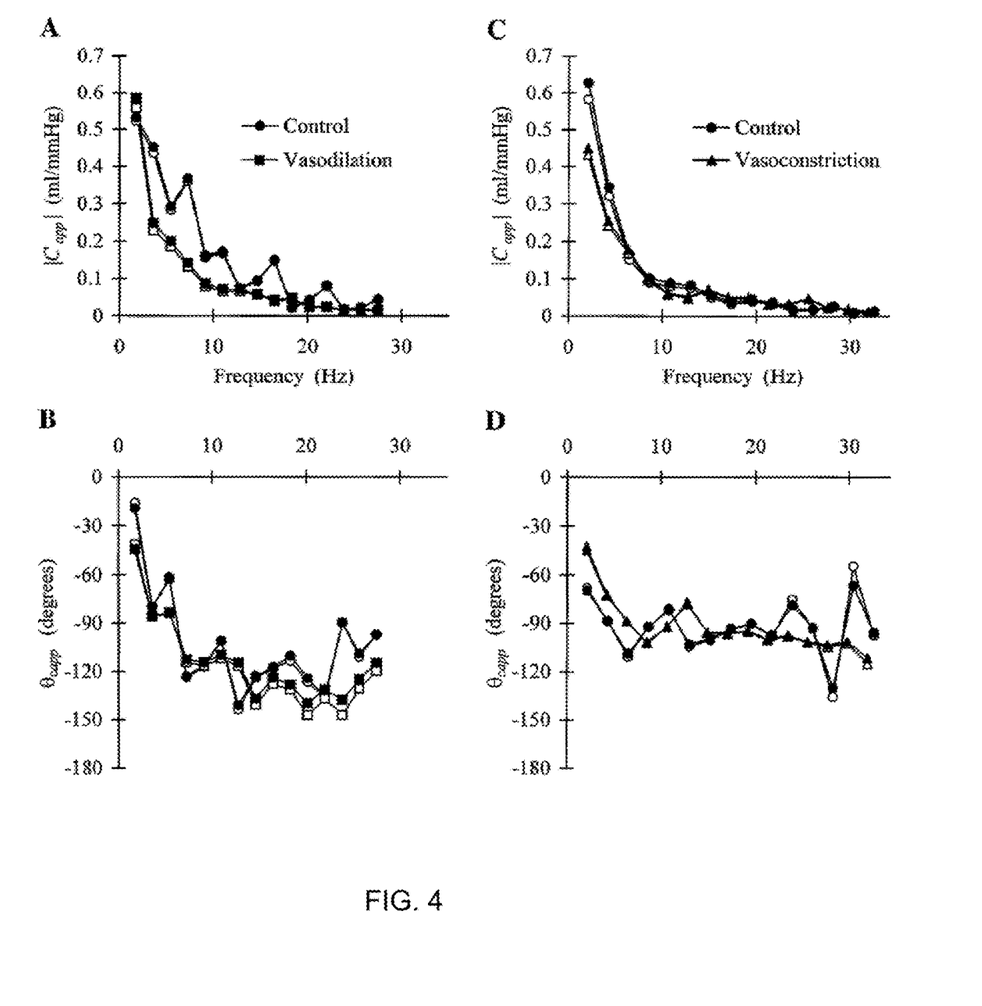
FIG. 4 includes four charts illustrating the relationship between arterial compliance and compliance phase.

As depicted in the Charts A-D of FIG. 4, from "Apparent Arterial Compliance" by Christopher M. Quick et al. in the American Journal of Physiology-Heart and Circulatory Physiology, Vol. 4, Issue 4, 1998, the entirety of which is incorporated by reference, one indicator of arterial compliance is the phase component of the Fourier transform of the pulse wave signal. Phase is a characteristic which can be measured directly from pulse signal non-invasively, thus making it a useful indicator for tracking compliance changes. Phase change detection can be a useful surrogate for actual compliance changes, particularly at low frequencies, preferably at frequencies of less than about 10 Hz, and more preferably at frequencies of less than about 5 Hz. At such frequencies, changes in compliance are also accompanied by marked changes in phase. For example, charts A and B depict the frequency dependent effects of a vasodilator on apparent arterial compliance. Chart A depicts the impact on apparent compliance magnitude and Chart B depicts the impact on apparent compliance phase. For both phase and magnitude, the changes are more pronounced at low frequencies. Similar pronounced amplitude and phase variations are visible in Charts C and D, which depict the impact of a vasoconstrictor.

Figure 5:
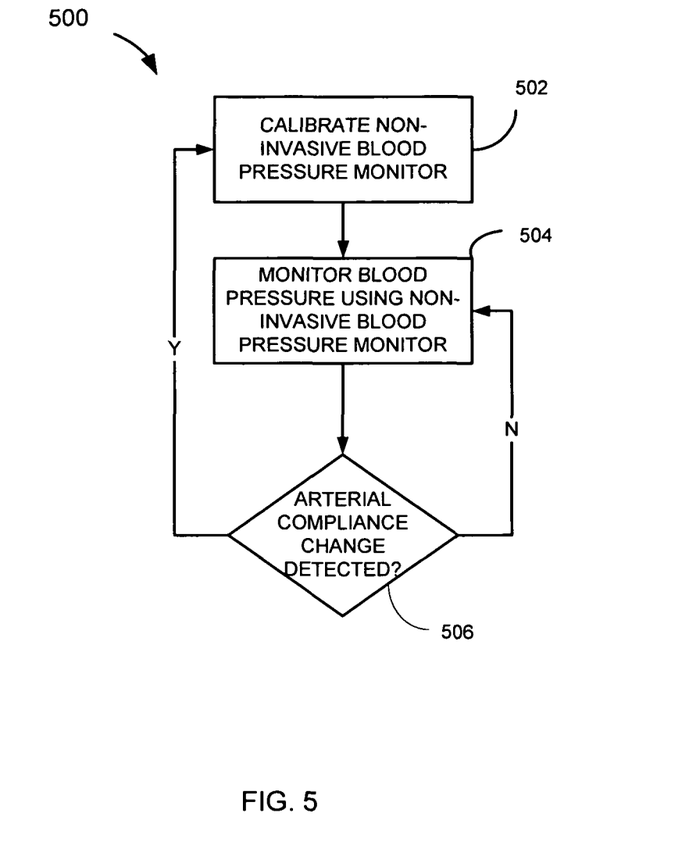
FIG. 5 is a flow chart of a method of monitoring blood pressure using the pulse oximetry system of FIG. 1 in accordance with an embodiment.

FIG. 5 is a flow chart of a method 500 of monitoring blood pressure using the pulse oximetry system 10 of FIG. 1 in accordance with an embodiment. The method begins with calibrating a non-invasive blood pressure monitor 15 incorporated into or in communication with the pulse oximetry system 10 (step 502). One illustrative method for calibrating the blood pressure monitor 15 is described further below in relation to FIG. 6. After calibration, the non-invasive blood pressure monitor 15 monitors the blood pressure of the patient for which it was calibrated (step 504) using pulse oximetry data collected by the pulse oximetry system 10. Suitable methods and systems for such monitoring, include, without limitation, those described in the patent and patent applications incorporated by reference above. While the blood pressure is being monitored, the blood pressure monitor 15 also monitors indicators of the arterial compliance of the patient. Suitable indicators include, for example, a phase component of the pulse signal generated by the pulse oximetry system 10 or a conditioned version thereof. If the blood pressure monitor 15 detects a change in the arterial compliance indicator that exceeds a threshold (DB 506), the blood pressure monitor 15 triggers a recalibration of the blood pressure monitor (step 502), for example using calibration device 80. Otherwise, the blood pressure monitor 15 continues to monitor blood pressure of the patient (step 504). Arterial compliance indicator monitoring is described farther below in relation to FIG. 7. In an embodiment, the blood pressure monitor 15 also stores a history of patient blood pressure and corresponding compliance indicator values.

Figure 6:
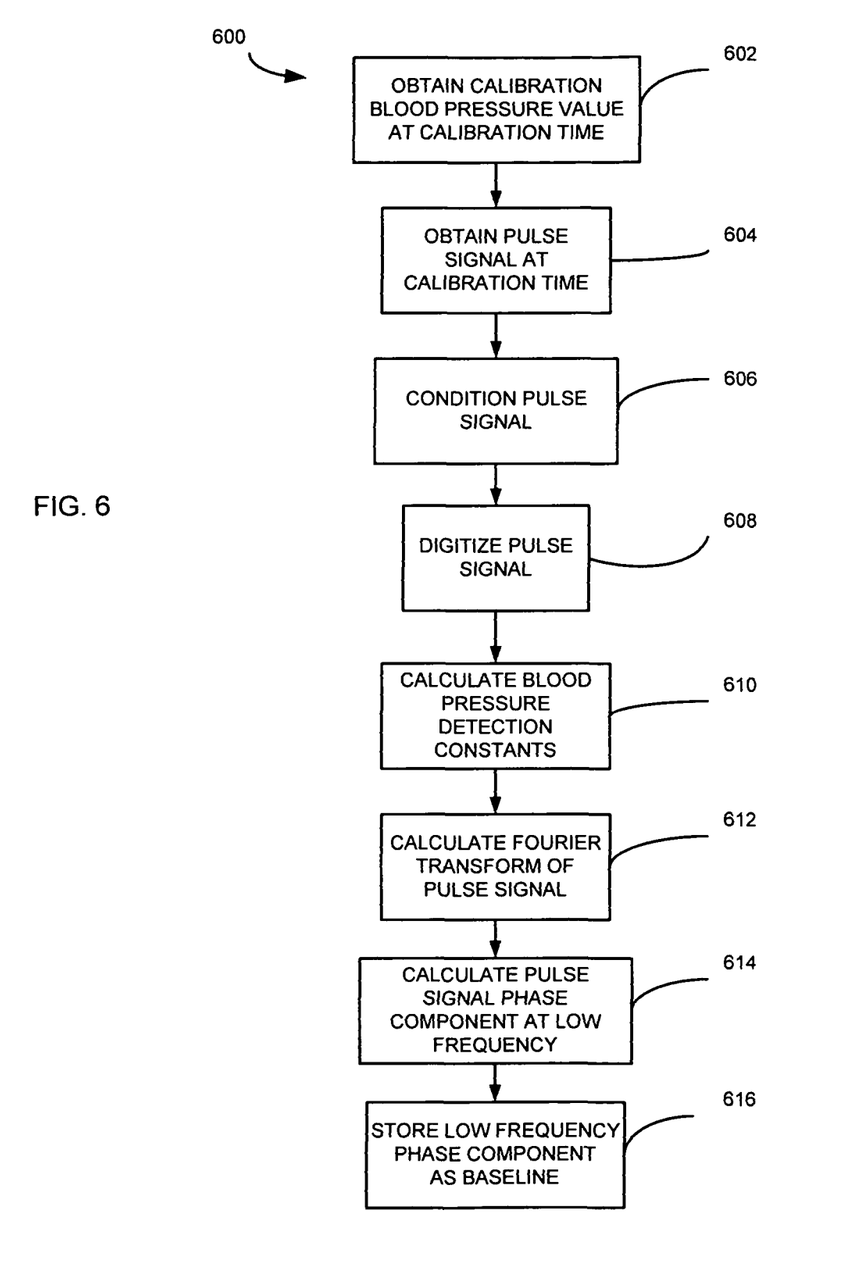
FIG. 6 is a flow chart of a method of calibrating a blood pressure monitoring system operating according to the method of FIG. 5 in accordance with an embodiment.

FIG. 6 is a flow chart of a method 600 of calibrating a blood pressure monitoring system operating according to the method of FIG. 5 in accordance with an embodiment. The method 600 begins with the blood pressure monitor 15 obtaining a baseline calibration blood pressure value at a calibration time (step 602). Preferably, the calibration blood pressure value includes both systolic and diastolic pressure values. At about the same time, the blood pressure monitor 15 obtains a pulse signal, such as a PPG signal from pulse oximetry system 10 (step 604).

The pulse signal, while still in analog form, is then optionally conditioned (step 606), for example by applying a low-pass or band-pass filter to remove noise from the signal. The conditioned signal is then digitized using an analog to digital converter (step 608). In an embodiment, in which the blood pressure monitor 15 is a separate device distinct from the pulse oximetry system 10, the conditioning and digitization of the signal is called out by the pulse oximetry system 10. In another such embodiment, the blood pressure monitor 15 receives a raw pulse signal and carries out the conditioning and digitization of the pulse signal itself. In embodiments in which the pulse oximetry system 10 and the blood pressure monitor 15 are incorporated into a single apparatus, the pulse signal is preferably conditioned and digitized before it is passed to the blood pressure monitoring components of the combined system.

Based on the conditioned and digitized pulse signal and the calibration blood pressure value, the blood pressure monitor calculates blood pressure monitoring constants (step 610) used to process pulse signal data into blood pressure values. Processes and algorithms for calculating these constants are described in U.S. Pat. No. 6,599,251, as well as in U.S. patent application Ser. No. 12/242,238, entitled "Systems and Methods For Non-Invasive Blood Pressure Monitoring," and filed on Sep. 30, 2008, each of which is incorporated above.

In addition, the blood pressure monitor calculates the Fourier transform of the conditioned, digitized pulse signal (step 612), e.g., using the discrete Fourier transform (DFT). In alternative embodiments, a Fourier transform of the original analog signal is calculated, instead. As known in the art, the Fourier transform of a signal yields both an amplitude component and phase component for the signal in the frequency domain. Based on the Fourier transform of the signal, the blood pressure monitor 15 obtains at least one Fourier phase component value (step 614) for the signal, preferably at a relatively low frequency. Suitable frequencies preferably include frequencies less than 10 Hz and more preferably less than about 5 Hz. The blood pressure monitor 15 stores the obtained phase component as a baseline phase component (step 616). It is this phase component that is used in detecting changes in arterial compliance (step 506).

Figure 7:
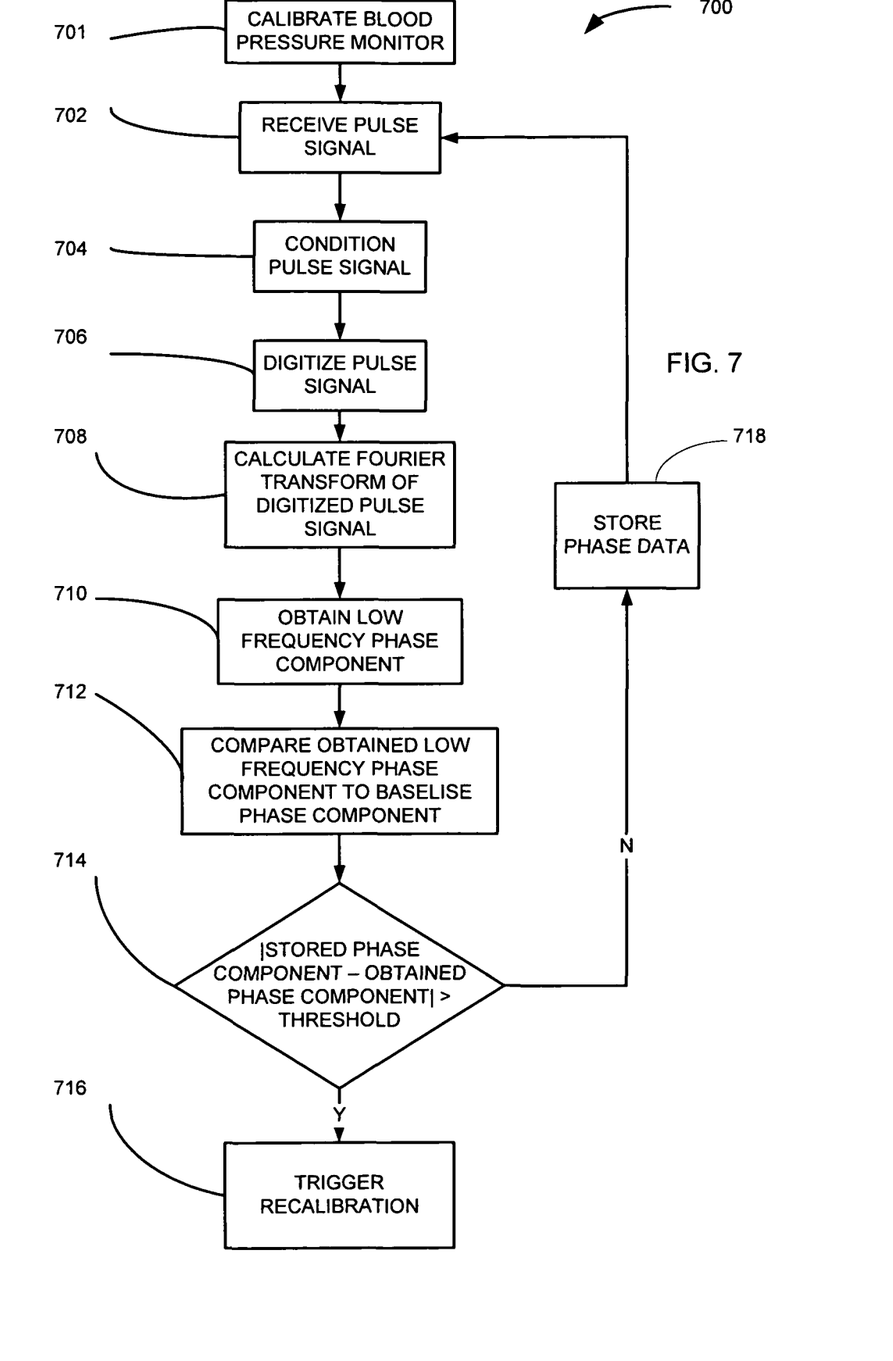
FIG. 7 is a flow chart of a method of maintaining calibration of the pulse oximetry system operating according to the method of FIG. 5 in accordance with an embodiment.

FIG. 7 is a flow chart of a method 700 of maintaining calibration of blood pressure monitor 15 operating according to the method of FIG. 5 in accordance with an embodiment. As mentioned above, one factor affecting blood pressure that may result in inaccuracies in pulse signal-based blood pressure measurements is arterial compliance. As described above, changes in arterial compliance can be detected by monitoring phase components of a pulse signal. The method 700 utilizes this principle to maintain the calibration of the blood pressure monitor 15.

The method 700 begins with the blood pressure monitor 15 calibrating itself (step 701), for example, as set forth above in relation to FIG. 6. After calibration, the blood pressure monitor 15 receives a pulse signal from a sensor monitoring the patient (step 702). The received pulse signal is conditioned (step 706) and digitized using an analog to digital converter (step 708). In one embodiment, in which the blood pressure monitor 15 is a separate device distinct from the pulse oximetry system 10, the conditioning and digitization of the signal is carried out by the pulse oximetry system 10. In another such embodiment, the blood pressure monitor 15 receives a raw pulse signal and carries out the conditioning and digitization of the pulse signal itself. In embodiments in which the pulse oximetry system 10 and the blood pressure monitor 15 are incorporated into a single apparatus, the pulse signal is preferably conditioned and digitized before it is passed to the blood pressure monitoring components of the combined system.

The blood pressure monitor 15 then calculates the Fourier transform of the digitized pulse signal, e.g., using the DFT (step 708). Alternatively, in other embodiments, the blood pressure monitor 15 calculates a continuous Fourier transform of the conditioned pulse signal. The blood pressure monitor 15, based on the Fourier transform, calculates at least one phase component of the pulse signal (step 710). Preferably, the phase component is calculated for a frequency in the range of preferably less than about 10 Hz, and more preferably less than about 5 Hz. The blood pressure monitor 15 compares the obtained phase component with a threshold change in phase (step 712). In certain embodiments, the threshold is determined based in part on the stored phase component obtained during calibration (step 701). For example, in an embodiment, the threshold is a predetermined percentage of the calibration phase. In another embodiment, the threshold is based on a history of phase data collected from the patient. For example, in one embodiment, the threshold is set to about a standard deviation of the phase since the prior calibration. In alternative embodiments, the threshold is a predetermined phase change, for example a fixed number of degrees or radians. The phase change used in the threshold comparison, in one embodiment, is calculated as follows:

Phase Change=|Stored Phase Component|−|Current Phase Component|.

At decision block 714, if the phase change is greater than the threshold, the blood pressure monitor 15 triggers a recalibration (step 716). If the phase change is less than the threshold, the blood pressure monitor stores the obtained phase data (step 718) and continues to monitor patient blood pressure (step 702). In alternative embodiments, upon calibration, one or more threshold phase values, as opposed to a phase change threshold, is computed and stored. In such embodiments, current phase values are compared directly to the stored threshold phase values.

In one embodiment, the method 700 is carried out by the blood pressure monitor 15 periodically. For example, the blood pressure monitor 15 carries out method 700 every 1 minute, every 2 minutes, every 5 minutes, or any other suitable period of time less than 1 minute or greater than 5 minutes. In one embodiment, the blood pressure monitor 15 carries out the method 700 substantially continuously.

What is claimed is:

1. A method for monitoring blood pressure comprising:
    storing a baseline signal phase component associated with a photoplethysmograph (PPG) signal obtained at a first point in time from a sensor comprising an emitter and detector;
    monitoring, using a processor, a current phase component of the PPG signal over a period of time subsequent to the first point in time;
    calculating, using the processor, a difference between the current phase component with the stored baseline phase component; and
    triggering, using the processor, a cuff-based blood pressure monitoring device to inflate an occluding cuff to obtain a blood pressure measurement at a second point in time in response to the calculated difference exceeding a threshold value.

2. The method of claim 1, comprising receiving the blood pressure measurement obtained at about the second point in time wherein the blood pressure measurement is determined independent of the PPG signal data.

3. The method of claim 2, comprising calibrating a continuous non-invasive blood pressure monitor based on the blood pressure measurement and the PPG signal obtained at the second point in time.

4. The method of claim 3, comprising calculating a monitored blood pressure value using a PPG signal at a time subsequent to the second point in time in response to the calculated difference falling below the threshold value.

5. The method of claim 3, further comprising recalibrating the continuous non-invasive blood pressure monitor, wherein the recalibrating comprises:
    obtaining, using the cuff-based blood pressure monitoring device, a second blood pressure measurement independent of PPG signal data at a third point in time, which is subsequent to the second point in time;
    calculating, using the processor, blood pressure calibration values based on a PPG signal obtained at about the third point in time and the second blood pressure measurement; and
    storing an updated baseline PPG signal phase component.

6. The method of claim 1, wherein calculating the difference between the current phase component with the stored baseline phase component comprises calculating the difference between the phase components at a signal frequency of less than about 5 Hz.

7. The method of claim 1, wherein calculating the difference between the current phase component with the stored baseline phase component comprises calculating the Fourier phase component of the PPG signal.

8. A blood pressure monitor comprising:
    a sensor for detecting a PPG signal from a patient, wherein the sensor comprises an emitter and detector;
    a memory for storing baseline signal phase components; and
    a processor configured to perform operations comprising:
        storing a baseline signal phase component derived from a PPG signal obtained at a first point in time;

monitoring a current phase component of the PPG signal over a period of time subsequent to the first point in time;

calculating a difference between the current phase component and the stored baseline phase component; and triggering a cuff-based blood pressure monitoring device to inflate an occluding cuff to obtain a blood pressure measurement at a second point in time in response to the calculated difference exceeding a threshold value.

9. The blood pressure monitor of claim 8, further comprising a pulse oximetry monitor coupled to the sensor.

10. The blood pressure monitor of claim 8, further comprising an input for receiving the blood pressure measurement at about the second point in time from the cuff-based blood pressure monitoring device.

11. The blood pressure monitor of claim 8, wherein the processor is further configured to perform operations comprising calibrating a continuous non-invasive blood pressure monitor based on the blood pressure measurement and the PPG signal obtained at the second point in time.

12. The blood pressure monitor of claim 8, wherein the processor is further configured to perform operations comprising:

obtaining a second blood pressure measurement at a third point in time, which is subsequent to the second point in time;

calculating blood pressure calibration values based on a PPG signal obtained at about the third point in time and the second blood pressure measurement; and storing an updated baseline signal phase component.

13. The blood pressure monitor of claim 8, wherein calculating the difference between the current phase component with the stored baseline phase component comprises calculating the difference between the phase components at a signal frequency of less than about 5 Hz.

14. The blood pressure monitor of claim 8, wherein calculating the difference between the current phase component with the stored baseline phase component comprises calculating the Fourier phase component of the PPG signal.

15. A computer readable medium storing computer readable instructions, which, when executed by a processor, cause the processor to a carry out a method comprising:

storing a baseline signal phase component associated with a photoplethysmograph (PPG) signal obtained at a first point in time from a sensor comprising an emitter and detector;

monitoring a current phase component of the PPG signal over a period of time subsequent to the first point in time;

calculating a difference between the current phase component with the stored baseline phase component; and triggering a cuff-based blood pressure monitoring device to inflate an occluding cuff to obtain a blood pressure measurement in response to the calculated difference exceeding a threshold value.

16. The computer readable medium of claim 15, wherein calculating the difference between the current phase component with the stored baseline phase component comprises calculating the difference between the phase components at a signal frequency of less than about 10 Hz.

17. The computer readable medium of claim 15, wherein calculating the difference between the current phase component with the stored baseline phase component comprises calculating the Fourier phase component of the PPG signal.

18. The method of claim 1, wherein calculating the difference between the current phase component with the stored baseline phase component comprises calculating the difference between the phase components at a signal frequency of less than about 10 Hz.

19. The blood pressure monitor of claim 8, wherein calculating the difference between the current phase component with the stored baseline phase component comprises calculating the difference between the phase components at a signal frequency of less than about 10 Hz.

20. The method of claim 1, wherein the baseline signal phase component and the current phase component are at a signal frequency of the PPG signal.

21. The blood pressure monitor of claim 8, wherein the baseline signal phase component and the current phase component are at a signal frequency of the PPG signal.

* * * * *